(12) United States Patent
Lee

(10) Patent No.: US 9,693,837 B2
(45) Date of Patent: Jul. 4, 2017

(54) DENTAL IMPLANT

(76) Inventor: Sue S. Lee, Framingham, MA (US)

( * ) Notice: Subject to any disclaimer, the term of this patent is extended or adjusted under 35 U.S.C. 154(b) by 437 days.

(21) Appl. No.: 12/536,948

(22) Filed: Aug. 6, 2009

(65) Prior Publication Data

US 2011/0033825 A1    Feb. 10, 2011

(51) Int. Cl.
*A61C 8/00* (2006.01)
*A61B 17/86* (2006.01)

(52) U.S. Cl.
CPC ........ *A61C 8/0018* (2013.01); *A61B 17/8625* (2013.01); *A61B 17/8685* (2013.01); *A61C 8/0043* (2013.01)

(58) Field of Classification Search
CPC ... A61C 8/0033; A61C 8/0018; A61C 8/0043; A61C 17/8625; A61C 17/8682
USPC ...................... 433/173–176, 201.1
See application file for complete search history.

(56) References Cited

U.S. PATENT DOCUMENTS

| | | | | |
|---|---|---|---|---|
| 2,258,207 A * | 10/1941 | Irwin | ............... | 433/173 |
| 3,797,113 A | 3/1974 | Brainin | | |
| 3,849,887 A | 11/1974 | Brainin | | |
| 3,881,251 A * | 5/1975 | Valen | ............... | 433/176 |
| 4,259,076 A * | 3/1981 | Yanney | ............... | 433/225 |
| 4,331,423 A * | 5/1982 | Yanney, Jr. | ............... | 433/225 |
| 4,360,343 A | 11/1982 | Hussein | | |
| 4,773,858 A * | 9/1988 | Marquez | ............... | 433/173 |
| 5,141,435 A * | 8/1992 | Lillard | ............... | 433/176 |
| 5,145,372 A * | 9/1992 | Daftary et al. | ............... | 433/173 |
| 5,316,478 A * | 5/1994 | Chalifoux | ............... | 433/221 |
| 5,370,695 A * | 12/1994 | Meuli et al. | ............... | 623/23.53 |
| 5,427,526 A * | 6/1995 | Fernandes | ............... | 433/173 |
| 5,427,527 A | 6/1995 | Niznick et al. | | |
| 5,435,723 A | 7/1995 | O'Brien | | |
| 5,489,210 A * | 2/1996 | Hanosh | ............... | 433/173 |
| 5,527,183 A | 6/1996 | O'Brien | | |
| 5,766,009 A * | 6/1998 | Jeffcoat | ............... | 433/173 |
| 5,816,812 A | 10/1998 | Kownacki et al. | | |
| 5,897,319 A | 4/1999 | Wagner et al. | | |
| 5,931,674 A * | 8/1999 | Hanosh et al. | ............... | 433/173 |
| 6,371,989 B1 * | 4/2002 | Chauvin et al. | ............... | 623/17.11 |
| 6,375,465 B1 * | 4/2002 | Engman et al. | ............... | 433/174 |
| 6,447,513 B1 * | 9/2002 | Griggs | ............... | 606/62 |
| 6,726,481 B1 | 4/2004 | Zickmann et al. | | |
| 6,962,574 B1 * | 11/2005 | Noblitt et al. | ............... | 604/60 |

(Continued)

OTHER PUBLICATIONS

International Search Report mailed Apr. 26, 2011 for International Application No. PCT/US2010/044554 (5 pages).

(Continued)

*Primary Examiner* — Cris L Rodriguez
*Assistant Examiner* — Hao D Mai
(74) *Attorney, Agent, or Firm* — Mintz Levin Cohn Ferris Glovsky and Popeo, P.C.; Kongsik Kim; Derek E. Constantine

(57) ABSTRACT

A dental implant system for supporting a cosmetic tooth prosthesis includes an elongated body adapted to be disposed in a jaw bone of a patient. The elongated body includes a distal end and a proximal end and extends along a longitudinal axis. The elongated body includes a tapered outer surface that tapers along the longitudinal axis distally from the proximal end of the elongated body. The outer surface of the tapered elongated body includes a plurality of barbs for securing the elongated body in the jaw bone of the patient.

15 Claims, 7 Drawing Sheets

(56) References Cited

U.S. PATENT DOCUMENTS

| | | | |
|---|---|---|---|
| 7,008,226 B2 | 3/2006 | Mayer et al. | |
| 7,300,282 B2 | 11/2007 | Sapian | |
| 7,338,286 B2 | 3/2008 | Porter et al. | |
| 7,846,162 B2 * | 12/2010 | Nelson et al. | 606/62 |
| 2003/0036036 A1 | 2/2003 | Porter et al. | |
| 2004/0010312 A1 * | 1/2004 | Enayati | 623/17.11 |
| 2004/0121286 A1 | 6/2004 | Aravena et al. | |
| 2006/0046229 A1 * | 3/2006 | Teich | 433/173 |
| 2006/0172258 A1 | 8/2006 | Niznick | |
| 2006/0228674 A1 * | 10/2006 | Marotta | 433/214 |
| 2007/0099152 A1 | 5/2007 | Busch et al. | |
| 2007/0254265 A1 | 11/2007 | Callan | |
| 2008/0124676 A1 * | 5/2008 | Marotta | 433/174 |
| 2008/0261175 A1 | 10/2008 | Hurson | |
| 2008/0280254 A1 | 11/2008 | Ackermann | |
| 2011/0269103 A1 * | 11/2011 | Shimko | 433/173 |

OTHER PUBLICATIONS

Written Opinion mailed Apr. 26, 2011 for International Application No. PCT/US2010/044554 (4 pages).

* cited by examiner

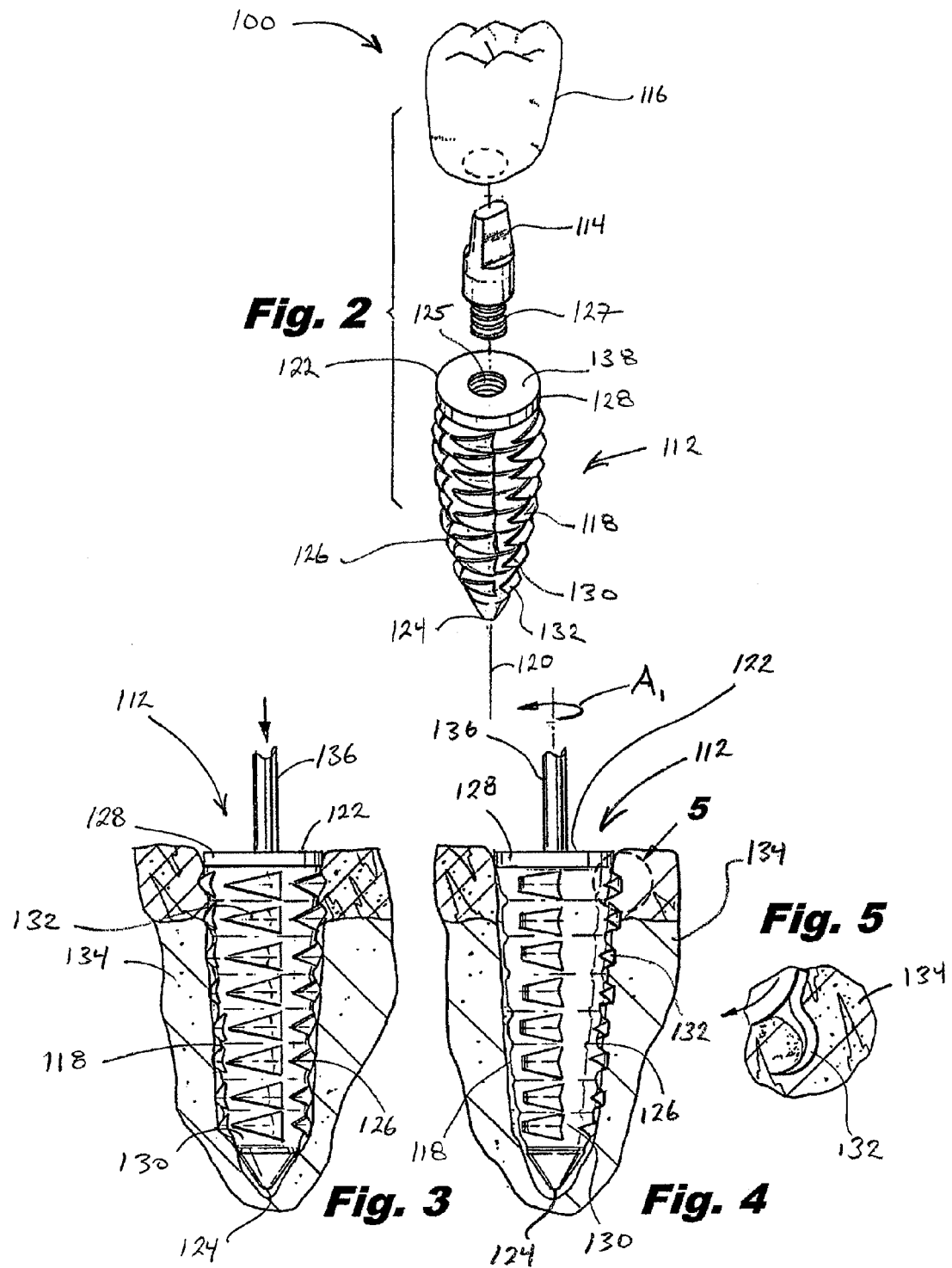

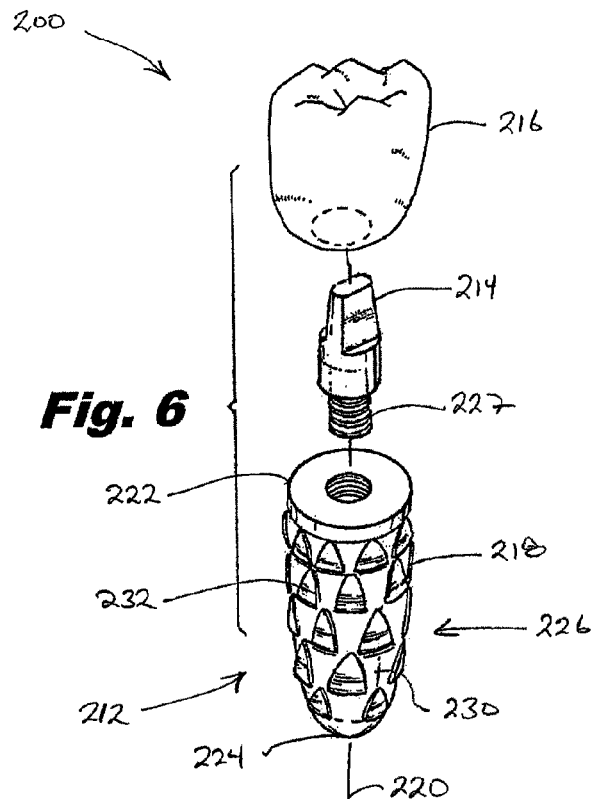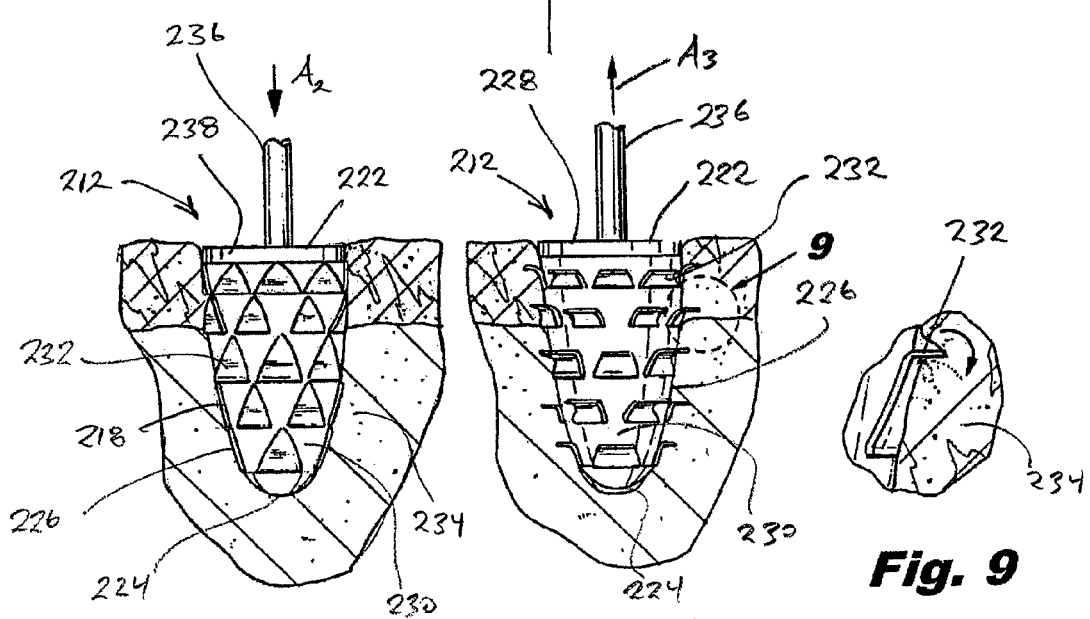

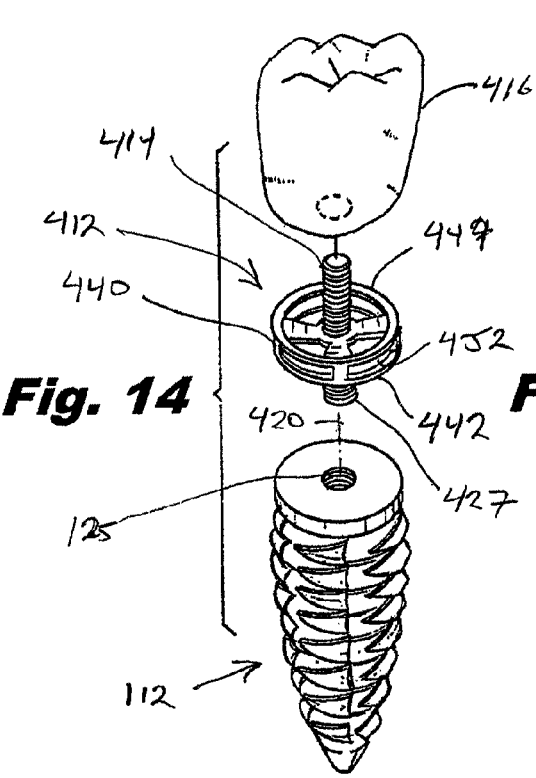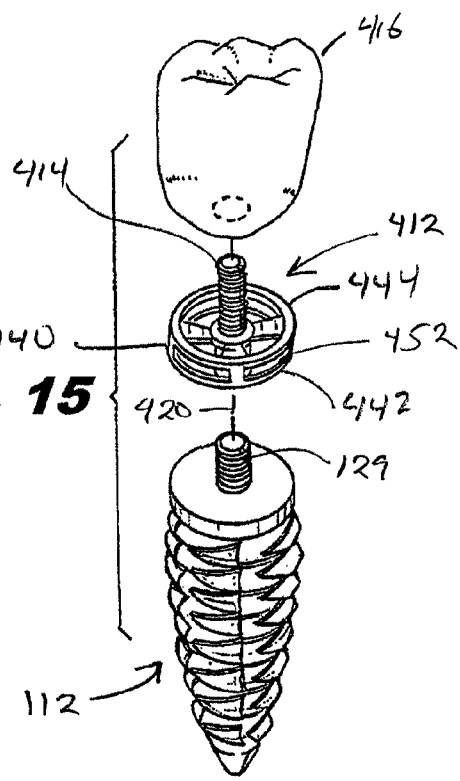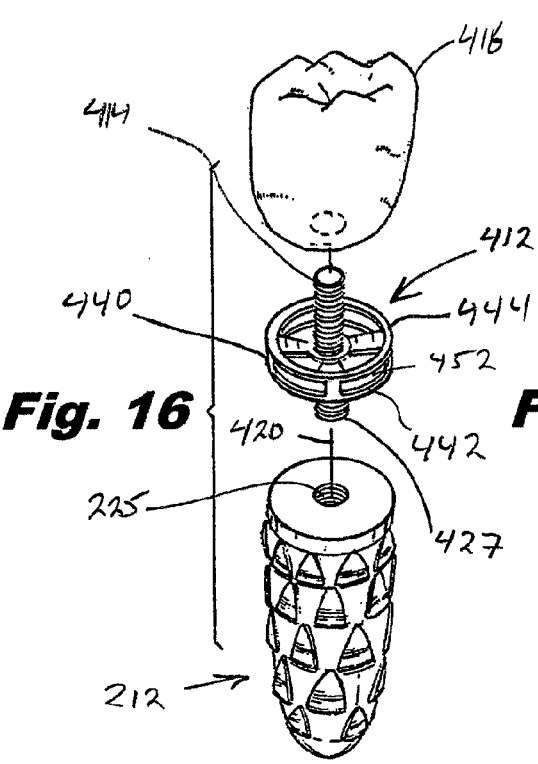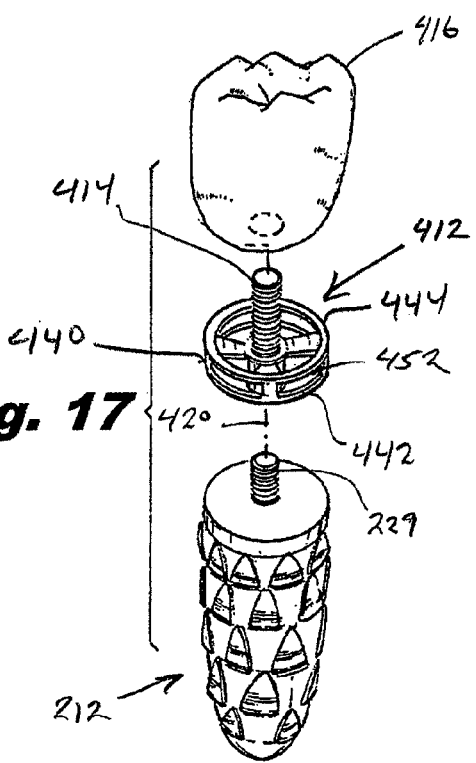

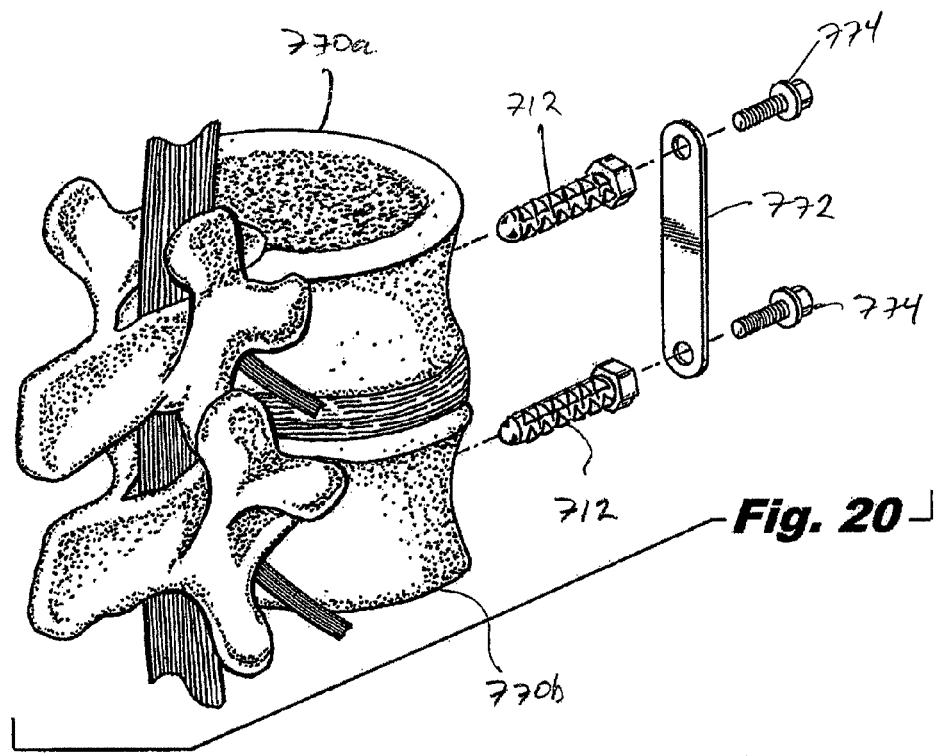
Fig. 20
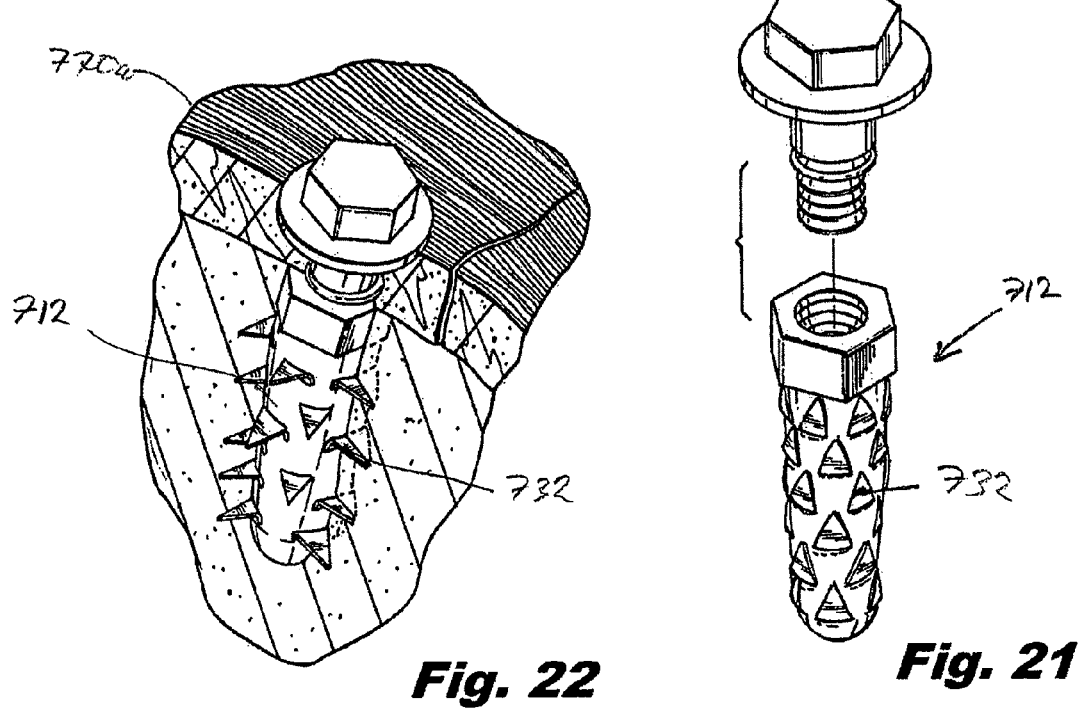
Fig. 22  Fig. 21

DENTAL IMPLANT

TECHNICAL FIELD

The present invention generally relates to the field of medical technology involving implants that are suitable for being implanted in bone tissue, and in particular to a dental implant assembly, abutments and related articles, and methods of using the same.

BACKGROUND INFORMATION

Traditionally, implant dentistry involves the restoration of one or more teeth in a patient's mouth using artificial components. Such artificial components typically include a dental implant, an abutment connected to the implant, and a prosthesis or artificial tooth secured to the abutment. The process for restoring a tooth is typically carried out in three stages.

The first stage involves implanting the dental implant into the living bone of a patient's jaw. The oral surgeon first accesses the patient's jaw bone through the patient's gingival or gum tissue and removes any remains of the tooth to be replaced. Next, the specific site in the patient's jaw where the implant is to be anchored is made or widened by drilling and/or reaming to accommodate the width of the dental implant to be implanted. Then, the dental implant is inserted into the hole in the jaw bone.

The dental implant itself is typically fabricated from pure titanium or a titanium alloy. Such materials are known to produce osseointegration of the implant fixture with the patient's jaw bone. Osseointegration is a process by which the living bone surrounding the implant will proliferate and grow into whatever spaces exist between the implant and the bone surfaces. In this way the newly generated bone tissue encases the implant to securely hold or anchor it in place.

The dental implant fixture typically included a body portion and a collar. The body portion is configured to extend into and osseointegrate with the alveolar bone and includes a hollow threaded bore through at least a portion of the body portion and extending out to the collar. The top surface of the collar typically lies flush with the crest of the jawbone bone. The hollow threaded bore typically receives a dental abutment, either directly or by virtue of a separate securing device such as an abutment screw. The abutment (e.g., a final abutment) typically lies on the top surface and extends through the soft tissue, which lies above the alveolar bone. Some dental implants have collars that extend above the crest of the jawbone and through the soft tissue. The abutment ultimately supports the final tooth prosthesis. The prosthesis is typically secured to the abutment either by a cement or other adhesive or by use of a fastener such as a screw.

After the implant is initially installed in the jaw bone, a healing screw (a cover) is secured over the exposed proximal end in order to seal the internal bore of the implant body. The patient's gums are then sutured over the screw covered implant to allow the implant site to heal and to allow desired osseointegration to occur. Complete osseointegration typically takes several months, ending this Stage 1 phase.

In the second stage, the surgeon reaccesses the implant fixture by making an incision through the patient's gum tissues. The healing cover screw is then removed, exposing the proximal end of the implant. The hollow threaded bore of the implant is thoroughly cleaned and dried. The surgeon then attaches a temporary cap secured by a cover screw, which is screwed directly through the healing cap into the hollow threaded bore of the implant. The gingival tissues are again closed around the cap and sutured in place. To accurately record the position, the orientation and the shape of the final abutment, the surgeon can take a mold or impression of the patient's mouth. The impression, which includes the implant abutment sites, is then sent to the laboratory and is used to create a plaster or stone model which is a direct duplication of the patient's mouth. This provides the information needed to fabricate the prosthetic replacement tooth or any required intermediate prosthetic components.

Based on the model from the second stage, the technician will construct the final restoration by: (1) removing the sutures; (2) removing the healing cap and the healing cap screw; (3) thoroughly cleaning and drying the exposed hollow threaded bore of the implant body; (4) screwing the solid abutment into the implant body's hollow threaded bore; and, (5) securing the final cosmetic prosthesis to the patient's mouth abutments with a dental adhesive cement.

Implants of various tapers and with various thread profiles are known in the art. For example, U.S. Pat. No. 5,427,527 describes a conical implant design that is placed into a cylindrical osteotomy site in order to induce bone compression at the coronal aspect of the implant, i.e. at its widest end. Other thread profiles and patterns are known in the art. The most common design involves a symmetrical, V-shaped appearance such as that illustrated in U.S. Pat. No. 5,897,319. A variable thread profile is disclosed in U.S. Pat. Nos. 5,435,723 and 5,527,183 which is mathematically optimized for stress transfer under occlusal loads. U.S. Pat. Nos. 3,797,113 and 3,849,887 describe dental implants with external thread-like features having a flat shelf facing the coronal end of the implant.

While such prior art dental implants have been successful, there is a continuing desire to improve a dental implant's ability to osseointegrate with the alveolar bone and to improve the stability of the dental implant within the alveolar bone.

SUMMARY OF THE INVENTION

It is therefore desirable to provide an implant suitable for implantation in bone tissue, in particular a dental implant, that is easy to install and has improved stability. It is particularly desirable to provide such implants that are both safe for the patient and can be easily adapted to a variety of different working conditions. The new implant assemblies are stable under a variety of different working conditions and can be used to provide cosmetic restoration of a tooth as well as in various medical techniques where orthopedic implants are used.

Implants according to the invention have improved osseointegration properties, which allows for earlier loading compared to existing implants. The surfaces of the implant according to the invention that are to contact the bone tissue or that are to be grown around by bone tissue or that are to be intergrown by bone tissue comprise a plurality of barbs that have growth-promoting and/or other properties having a positive effect on biological integration of the implant in the vital issue. Furthermore, neither the implant according to the invention, nor its implantation is no more complicated than is the case for implants according to the state of the art.

A particular exemplary embodiment of the present invention relates to a dental implant system for supporting a cosmetic tooth prosthesis. The implant includes an elongated body adapted to be disposed in a jaw bone of a patient. The elongated body includes a distal end and a proximal end, and extends along a longitudinal axis. The elongated body includes a tapered outer surface that tapers along the longitudinal axis distally from the proximal end and includes a plurality of barbs for securing the elongated body in the jaw bone of the patient.

In alternative embodiments of the invention, the plurality of barbs are radially aligned on the tapered outer surface such that the plurality of barbs are secured in the jaw bone of the patient by rotating the elongated body about the longitudinal axis. The plurality of barbs can also be longitudinally aligned on the tapered outer surface such that the plurality of barbs are secured in the jaw bone of the patient by proximal movement of the elongated body. Alternatively, the plurality of barbs are mechanically deployable to secure the plurality of barbs in the jaw bone of the patient.

In another aspect of the invention, the elongated body of the dental implant defines a threaded bore extending distally from the proximal end for receiving an abutment configured to receive a cosmetic tooth prosthesis. The abutment can include a threaded screw member for screwing into a threaded bore defined by the elongated body member. Alternatively, the elongated body can include a threaded post extending from the proximal end for receiving the abutment that defines a threaded bore, the threaded bore configured to be screwed onto a threaded post extending from the proximal end of the elongated body. The abutment can include a substantially cylindrical base portion with a post coupled to the substantially cylindrical base portion, and the substantially cylindrical base portion can include a plurality of apertures to allow cleaning of the cosmetic tooth prosthesis.

In yet another aspect of the present invention, a dental implant system for supporting a cosmetic tooth prosthesis includes a substantially cylindrical base portion, a plurality of prongs extending away from the substantially cylindrical base portion adapted to be disposed in a gingival tissue of a patient, and a post coupled to the substantially cylindrical base portion configured to receive a cosmetic tooth prosthesis. Each of the plurality of prongs can include a plurality of barbs for securing the plurality of prongs in the gingival tissue of the patient. The substantially cylindrical base portion can include a plurality of apertures to allow cleaning of the cosmetic tooth prosthesis.

BRIEF DESCRIPTION OF THE DRAWINGS

A fuller understanding of the aspects, objects, features, and advantages of certain embodiments according to the invention will be obtained and understood from the following description when read together with the accompanying drawings, which primarily illustrate the principles of the invention and embodiments thereof. The drawings are not necessarily to scale and like reference characters denote corresponding or related parts throughout the several views. The drawings and the disclosed embodiments of the invention are exemplary only and not limiting on the invention.

FIG. 2 is an exploded perspective view of one exemplary embodiment of a dental implant assembly in accordance with the invention.

FIG. 3 is a side view of the dental implant of FIG. 2 shown partially installed in the jaw bone of a patient.

FIG. 4 is a side view of the dental implant of FIG. 3 shown fully installed in the jaw bone of the patient such that the barbs are engaged in the bone tissue.

FIG. 5 is an enlarged top view showing one of the barbs of FIG. 4 engaged in the bone tissue.

FIG. 6 is an exploded perspective view of an alternative embodiment of a dental implant assembly in accordance with the invention.

FIG. 7 is a side view of the dental implant of FIG. 6 shown partially installed in the jaw bone of a patient.

FIG. 8 is a side view of the dental implant of FIG. 7 shown fully installed in the jaw bone of the patient such that the barbs are engaged in the bone tissue.

FIG. 9 is an enlarged side view showing one of the barbs of FIG. 8 engaged in the bone tissue.

FIG. 14 is an exploded perspective view of an alternative embodiment of a dental implant assembly in accordance with the invention.

FIG. 15 is an exploded perspective view of an alternative embodiment of a dental implant assembly in accordance with the invention.

FIG. 16 is an exploded perspective view of an alternative embodiment of a dental implant assembly in accordance with the invention.

FIG. 17 is an exploded perspective view of an alternative embodiment of a dental implant assembly in accordance with the invention.

FIG. 20 is an exploded perspective view of one exemplary embodiment of a bone implant in accordance with the invention being used to fuse two vertebrae.

FIG. 21 is an exploded perspective view of an alternative embodiment of a bone implant in accordance with the invention.

FIG. 22 is a perspective view of the bone implant of FIG. 21 shown fully installed in the bone tissue of a patient such that the barbs are engaged in the bone tissue.

DESCRIPTION

Figure 1:
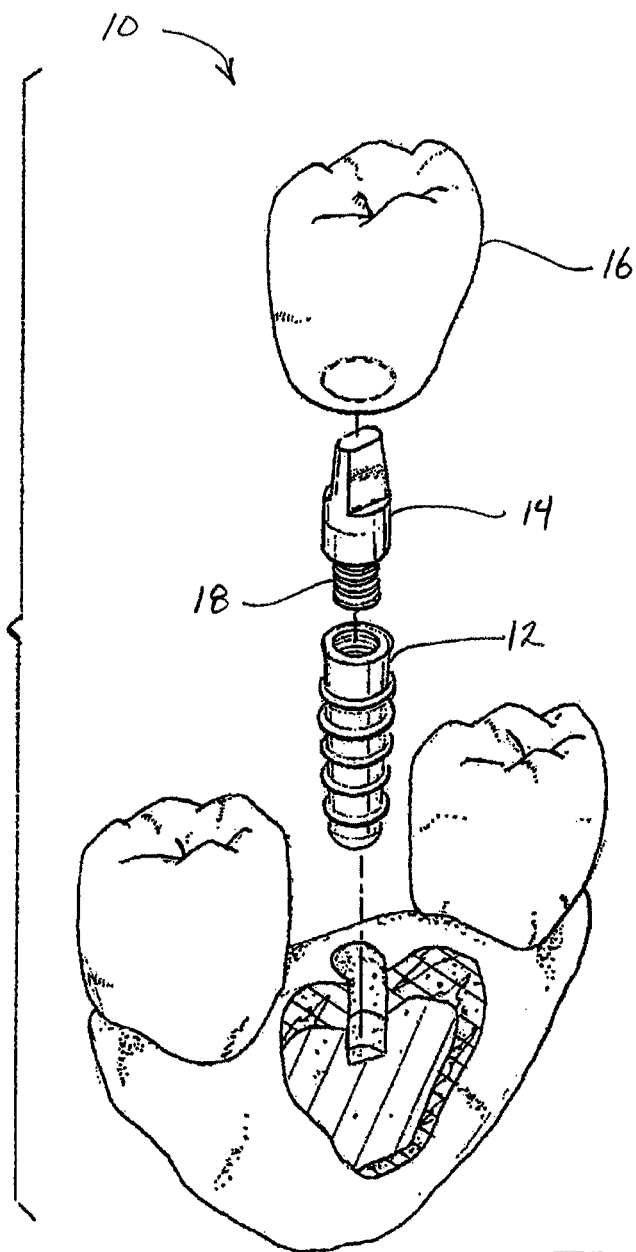
FIG. 1 is an exploded perspective view of a typical prior art dental implant assembly.

As indicated above, the present invention relates to the field of medical technology involving implants that are suitable for being implanted in bone tissue and methods of using the same. FIG. 1 depicts a dental implant assembly 10 of the prior art. The assembly 10 includes an implant 12, an abutment 14, and a cosmetic tooth prosthesis 16. In use, the prior art implant 12 is inserted into a living jaw bone of a patient, after the insertion site is properly prepared by the oral surgeon. After removal of any remains of the tooth to be replaced, the specific site in the patient's jaw where the implant is to be anchored is made or widened by drilling and/or reaming to accommodate the width of the dental implant to be implanted. Then, the dental implant is inserted into the hole in the jaw bone. Next, the abutment 14 is attached to the implant 12 by virtue of the threaded post 18. An impression of the site and surrounding portions of the mouth may be taken at this point for use in creating a final prosthesis 16. A temporary prosthesis (not shown) is typically attached to the abutment 14 or directly into the implant 12 and left in place while the gums heal and while the jaw bone further osseointegrates with the implant 12. At a later point, the temporary prosthesis is removed and replaced by a final prosthesis 16 prosthesis that is secured to the abutment 14 with a dental adhesive cement.

Referring now to FIGS. 2-5, a dental implant assembly 100 according to one exemplary embodiment of the present invention is shown. The assembly 100 generally includes an implant 112, an abutment 114, and a cosmetic tooth prosthesis 116. In this embodiment, the implant 112 comprises an elongated body portion 118, which extends along a longitudinal axis 120 and includes a proximal end 122 and a distal end 124. The elongated body 118 defines a bore 125 extending distally from the proximal end 122 for receiving a post 127 of the abutment 114. The bore 125 and the post 127 can be threaded so that that abutment 114 can be easily screwed into the implant 112. The terms proximal and distal require a point of reference. In this application, the point of reference is the perspective of the operator (e.g., oral surgeon, dentist, lab technician, etc.) who would insert the disclosed medical device into the patient. Therefore, the term proximal will always refer to an area closest to the operator, whereas distal will always refer to an area away from the operator.

The elongated body portion 118 includes a lower portion 126 and collar 128 located near the proximal end 122. The lower portion 126 is tapered and includes an outer surface 130 configured to promote osseointegration. The outer surface 130 includes a plurality of unbarbed, unidirectional, hook-like projections 132 which can be physically anchored in the tissue 134 of the jaw bone (e.g., see FIG. 5). As shown, the lower portion 126 is illustrated as being generally conical or tapered. However, in other embodiments, the lower portion 126 can be substantially cylindrical or otherwise shaped. The dental implant 112 can be made of titanium, a titanium alloy, or although other materials such as, for example, various types of ceramics.

The outer surface 130 can be coated or otherwise treated to further promote osseointegration. In one embodiment, the outer surface 130 and/or the plurality of projections 132 can be roughened in several different manners, such as, for example, by acid-etching, grit blasting, bead blasting, or other types of mechanical or physical texturing, to increase the surface area of the lower portion 126. Alternatively, the outer surface 130 can coated with a substance in order to promote osseointegration. In some embodiments, this may result in decreasing or increasing the surface area of the lower portion 126. Calcium phosphate ceramics, such as tricalcium phosphate (TCP) and hydroxyapatite (HA) are examples of materials that can enhance osseointegration by changing the chemistry of the outer surface 130.

In other embodiments, the outer surface 130 and/or the plurality of projections 132 can comprise macroscopic structures, such as, for example, threads, micro-threads, indentations, and/or grooves that are configured to promote osseointegration and can be used alone or combined with the roughening and/or the coatings described above. In one embodiment, the outer surface 130 comprises a microstructure surface, such as, a highly crystalline and phosphate enriched titanium oxide microstructured surface with open pores in the low micrometer range. An example of such a surface is sold under the trademark, TiUnite™ by Nobel Biocare A™. All of the surface treatments and techniques described above can be used alone or in combination with each other to promote osseointegration. For example, a zirconium ceramic body can be coated with porous zirconium to provide a microstructure surface, which can then be coated with a substance configured to promote osseointegration.

The process of installing the dental implant assembly 100 according to one exemplary embodiment of the present invention includes accesses the patient's jaw bone through the patient's gingival or gum tissue and removing any remains of the tooth to be replaced. Next, the specific site in the patient's jaw where the implant is to be anchored is made or widened by drilling and/or reaming to accommodate the width/diameter of the a lower portion 126. Then, the elongated body 118 is inserted into the hole in the jaw bone. When the elongated body 118 is properly positioned, an insertion tool 136 is inserted into the bore 125 and rotated in a clockwise direction (indicated by arrow $A_1$ in FIG. 4) to anchor the projections 132 in the tissue 134 of the jaw bone. When the implant 112 is no longer needed or if it is not properly positioned, it can be removed by grasping the elongated body 118 with the insertion tool 136 and simultaneously withdrawing the elongated body 118 while turning the insertion tool 136 in a counterclockwise direction to disengage the projections 132.

After the implant 112 has been properly installed in the jaw bone of the patient, the top surface 138 of the collar 128 (proximal end 122 of the elongated body portion 118) is typically flush with the patient's gingival or gum tissue. In alternative embodiments, the top surface 138 of the collar 128 can be positioned flush with the crest of the jaw bone. As described above, an abutment 114 can then be installed by screwing the treaded post 127 of the abutment 114 into the hollow threaded bore 125 of the elongated body portion 118. A temporary or final permanent tooth prosthesis 116 can then be secured to the abutment 114 with a dental adhesive cement. A variety of mechanical fasteners and/or adhesives can be use to secure the abutment 114 to the implant 112 and the tooth prosthesis 116 to the abutment without departing from the scope of the invention.

Referring now to FIGS. 6-9, a dental implant assembly 200 according to an alternative embodiment of the present invention is shown. The dental implant assembly 200 performs substantially the same function as the dental implant assembly 100 described above, and therefore like reference numerals preceded by the numeral "2" are used to indicate like elements. The assembly 200 generally includes an implant 212, an abutment 214, and a cosmetic tooth prosthesis 216. In this embodiment, the implant 212 comprises an elongated body portion 218, which extends along a longitudinal axis 220 and includes a proximal end 222 and a distal end 224. The elongated body 218 defines a bore 225 extending distally from the proximal end 222 for receiving a post 227 of the abutment 214. The bore 225 and the post 227 can be threaded so that that abutment 214 can be easily screwed into the implant 212.

The elongated body portion 218 includes a lower portion 226 and collar 228 located near the proximal end 222. The lower portion 226 is tapered and includes an outer surface 230 configured to promote osseointegration. The outer surface 230 includes a plurality of unbarbed, unidirectional, hook-like projections 232 which can be physically anchored in the tissue 234 of the jaw bone (e.g., see FIG. 9). As shown, the lower portion 226 is illustrated as being generally conical or tapered. However, in other embodiments, the lower portion 226 can be substantially cylindrical or otherwise shaped. The dental implant 212 can be made of titanium, a titanium alloy, or although other materials such as, for example, various types of ceramics. As described above, the outer surface can be coated or otherwise treated to further promote osseointegration.

The process of installing the dental implant assembly 200 is similar to the installation procedure described above with respect to the dental implant assembly 100 described above. After the specific site in the patient's jaw where the implant is to be anchored is prepared, the elongated body 218 is inserted into the hole in the jaw bone. When the elongated body 218 is properly positioned, an insertion tool 236 is inserted into the bore 225 and forced distally (indicated by Arrow $A_2$ in FIG. 7), and then pulled proximally (in-dicated by Arrow $A_3$ in FIG. 8) to anchor the projections 232 in the tissue 234 of the jaw bone (FIG. 9).

In alternative embodiments, the dental implant assemblies 100, 200 can include an actuating mechanism to mechanically deploy the projections 132, 232 into the tissue 134, 234 of the jaw bone or adjust the amount of opening of the projections 132, 232. The actuating mechanism can be externally located from the dental implant 112, 212 or located within the implant 112, 212. For example, in one embodiment, the actuating mechanism can wirelessly communicate (e.g., radio frequency, infrared, microwave, etc.) with the implant 112, 212 allowing the oral surgeon to open and close the projections 132, 232 remotely. In another embodiment, the insertion tool 136, 236 (or similar device) can be mechanically coupled to actuating mechanism connector, which is used mechanically adjust the amount of opening of the projections 132, 232. For example, the actuating mechanism connector can be a screw and the insertion tool 136, 236 used to rotate the screw, thereby applying torque to a portion of the implant 112, 212 to open/close the projections 132, 232. The actuating mechanism connector can alternatively be a lever. The insertion tool 136, 236 can be used to rotate or push the lever in various directions to change the opening amount of the projections 132, 232. Alternatively, the projections 132, 232 can include a protrusion (not shown) on their interior surface that can be directly engaged by the insertion tool 136, 236 to force the projections 132, 232 in an outward direction.

Figure 10:
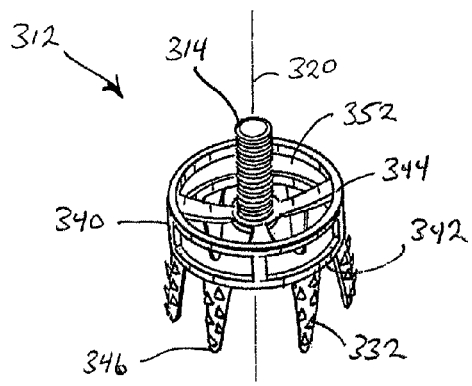
FIG. 10 is perspective view of an alternative embodiment of a dental implant in accordance with the invention.
Figure 11:
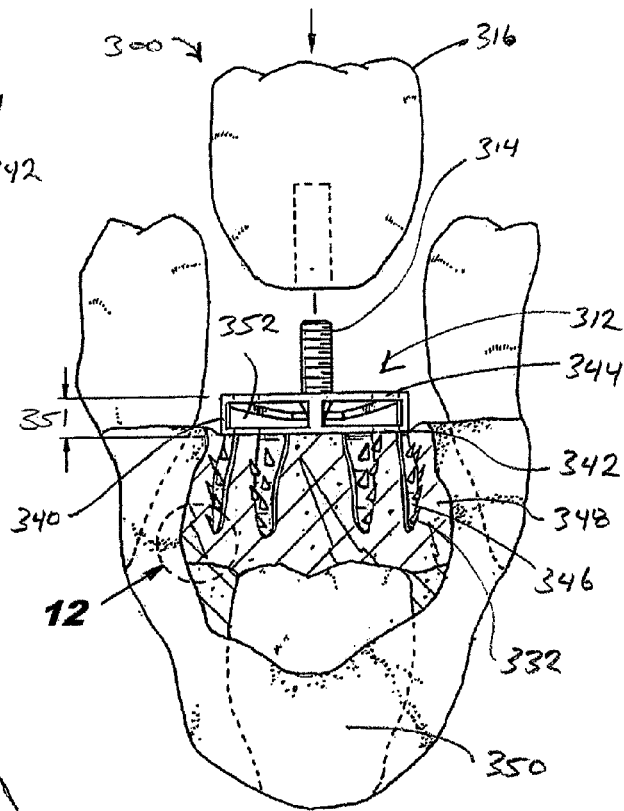
FIG. 11 is an exploded side view showing the dental implant of FIG. 10 installed in the gingival tissue of the patient.
Figure 12:
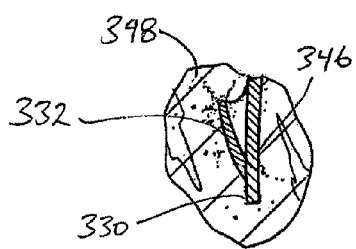
FIG. 12 is an enlarged side view showing one of the barbs of FIG. 11 engaged in the gingival tissue.

Referring now to FIGS. 10-12, a dental implant assembly 300 according to an alternative embodiment of the present invention is shown. The assembly 300 generally includes a temporary implant 312 and a cosmetic tooth prosthesis 316. In one embodiment, the temporary implant 312 comprises a base portion 340, which includes a lower portion 342, an upper portion 344, and a plurality of prongs 346 extending distally away from the lower portion 342. The plurality of prongs 346 are adapted to be disposed in the gingival tissue of a patient (e.g., see FIG. 12) and each of the plurality of prongs 346 include a plurality of unidirectional projections 332 disposed an outer surface 330 of the projections 332. As shown, the plurality of prongs 342 are disposed around the perimeter of the base portion 340, however, in other embodiments, prongs 342 can be disposed at additional or alternative locations (e.g., in the interior region of the base portion 340).

The temporary implant 312 also includes and an abutment post 314 coupled to the base portion 340 configured to receive a cosmetic tooth prosthesis. As shown, the abutment post 314 is disposed at the central axis 320 of the implant 312, however, the abutment post 314 could be offset from the central axis 320 in alternative embodiments to accommodate the tooth prosthesis 316.

The dental implant assembly 300 is often used for children who have lost a tooth, or where a tooth did not come in, in order to maintain adequate space for adult teeth to grow in. Thus, the process of installing the dental implant assembly 300 according to one exemplary embodiment of the present invention does not required accessing the patient's jaw bone through the patient's gingival or gum tissue as described above with respect to the dental implant assemblies 100 and 200. The temporary implant 312 is positioned at the specific site in the patient's jaw where the dental implant assembly 300 is to be anchored and the plurality of prongs 346 forced distally into the patient's gingival or gum tissue 348 until the lower portion 342 is flush with the patient's gingival or gum tissue 348. When the implant 312 is no longer needed, it can be removed by a process similar to a tooth extraction. Alternatively, as the new tooth 350 grows in, the new tooth 350 itself will force the implant 312 out of the patient's gingival tissue 348.

After the implant 312 has been properly installed in the gingival tissue 348 of the patient, a tooth prosthesis 316 can then be secured to the abutment post 314 with a dental adhesive cement as described above. A variety of mechanical fasteners and/or adhesives can be use to secure the tooth prosthesis 316 to the abutment post 314 without departing from the scope of the invention. For example, the abutment post 314 can be threaded and the tooth prosthesis 316 can be screwed onto the implant abutment post 314. As shown, the top portion 344 is elevated proximally (as indicated by reference numeral 351) from the gingival tissue 348. This proximal elevation can, for example, allow for easier cleaning of the implant assembly 300 by the patient, dentist, hygienists, etc. Additionally, the base portion 340 can define one or more apertures 352 to provide additional access for cleaning the implant assembly 300. In alternative embodiments, the top base portion 340 can be configures such that the cosmetic tooth prosthesis 316 is flush with the crest of the gingival tissue 348.

Figure 13:
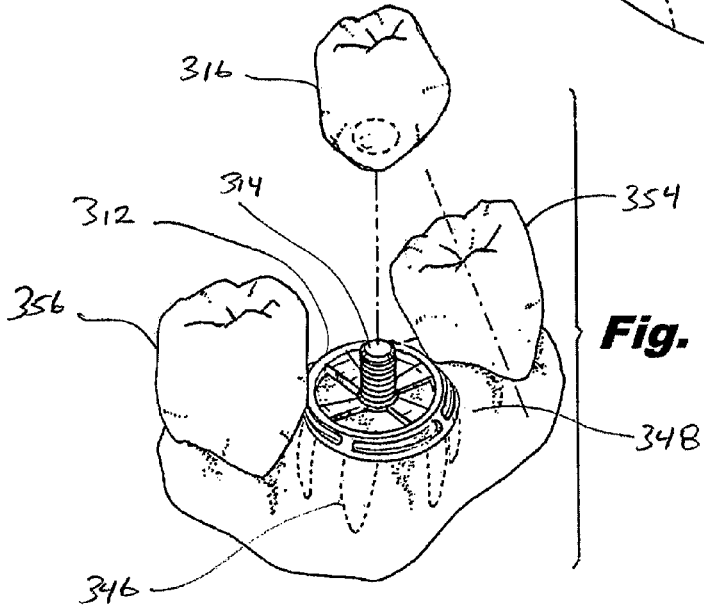
FIG. 13 is an exploded perspective view showing an alternative use of the dental implant of FIG. 10.

Referring now to FIG. 13, the dental implant assembly 300 is shown positioned between two teeth 354, 356 as a spacer to ensure adequate space for a new tooth to grow in. As shown, one tooth 354 has begun to grow toward the other tooth 356 and could eventually prevent a new tooth from growing in properly. In this exemplary embodiment, the temporary implant 312 is positioned in the patient's gingival tissue 348 between the teeth 354, 356 and a temporary cosmetic tooth prosthesis 316 is being installed on the abutment post 314. The temporary cosmetic tooth prosthesis 316 can be, for example, an inexpensive stainless steel cosmetic tooth prosthesis. An inexpensive, temporary, tooth prosthesis can be shaped to fit virtually any situation, which allows the space for a new tooth to be maintained without expensive and time consuming orthodontia.

Referring now to FIGS. 14-17, an abutment 412 incorporating features of the temporary implant 312 is shown. In one embodiment, the abutment 412, comprises a base portion 440, which includes a lower portion 442 and an upper portion 444. The abutment 412 also includes and an abutment post 414 coupled to the base portion 440 configured to receive a cosmetic tooth prosthesis 416. As shown, the abutment post 414 is disposed at the central axis 420 of the abutment 412, however, the abutment post 414 could be offset from the central axis 420 in alternative embodiments to accommodate the tooth prosthesis 416.

After an implant 112, 212 has been properly installed in the jaw bone of the patient as described above, the abutment 412 can then be installed by screwing a treaded post 427 of the abutment 412 into the hollow threaded bore 125, 225 of the implant 112, 212 (FIGS. 14 and 16) or alternatively, the abutment 412 can include a hollow threaded bore (not shown) that is threaded onto threaded post 129, 229 in the implant 112, 212 (FIGS. 15 and 17). A temporary or final permanent tooth prosthesis 416 can then be secured to the abutment post 414 with a dental adhesive cement. A variety of mechanical fasteners and/or adhesives can be use to secure the abutment 414 to the implant 112, 212 and the tooth prosthesis 416 to the abutment without departing from the scope of the invention. For example, the abutment post 414 can be threaded and the tooth prosthesis 416 can be screwed onto the implant abutment post 414. As shown, the upper portion 444 is elevated proximally from the implant 112, 212. This proximal elevation can, for example, allow for easier cleaning by the patient, dentist, hygienists, etc. Additionally, the base portion 440 can define one or more apertures 452 to provide additional access for cleaning.

Figures 18, 19:
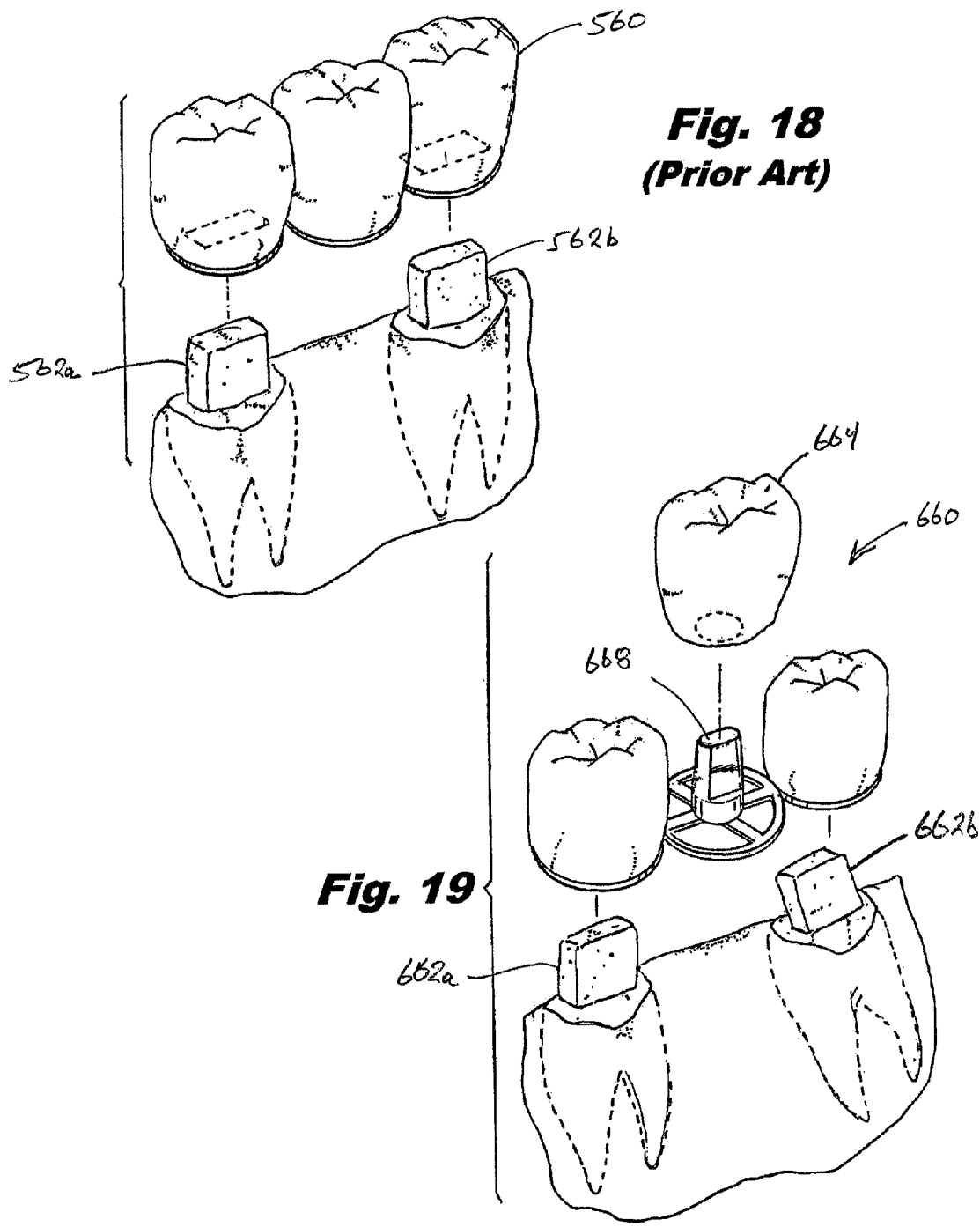
FIG. 18 is an exploded perspective view of a typical prior art dental bridge assembly.
FIG. 19 is an exploded perspective view of one exemplary embodiment of a dental bridge assembly in accordance with the invention.

Referring now to FIGS. 18 and 19, features of the present invention can be used for bridge assemblies. A bridge, also known as a fixed partial denture, is a dental restoration used to replace a missing tooth by joining permanently to adjacent teeth or dental implants. There are different types of bridges, depending on how they are fabricated and the way they anchor to the adjacent teeth. Conventionally, bridges are made using the indirect method of restoration however, bridges can be fabricated directly in the mouth using such materials as composite resin.

As shown in FIG. 18, a bridge 560 is fabricated by reducing the teeth on either side of the missing tooth or teeth by a preparation pattern determined by the location of the teeth and by the material from which the bridge is fabricated. In other words, the abutment teeth 562a and 562b are reduced in size to accommodate the material to be used to restore the size and shape of the original teeth in a correct alignment and contact with the opposing teeth. The materials used for the bridges include gold, porcelain fused to metal, or in the correct situation porcelain alone. The amount and type of reduction done to the abutment teeth varies slightly with the different materials used. The preparations for multiple-unit bridges 560 must possess proper taper and alignment to facilitate the insertion of the prosthesis 560 onto the abutment teeth 562a, 562b simultaneously. Thus, the taper of the abutment teeth 562a, 562b must match in order to properly seat the prosthesis 560; this is known as requiring parallelism among the abutments 562a, 562b.

When parallelism among the abutments is not possible, due to severe tipping of one of more of the abutment teeth, for example, a modified bridge assembly 660 may be useful, as shown in FIG. 19. After the abutment teeth 662a, 662b have been properly prepared, the bridge assembly 660 can be cemented first on to one of the abutments 662a or 662b, and then the other abutment 662a, 662b depending on the particular situation. Finally, an artificial tooth prosthesis 664 can then be inserted onto the abutment 668 of the bridge assembly 660.

Referring now to FIGS. 20-22, implants according to the present invention can also be used for various medical techniques where orthopedic implants are used. As shown in FIG. 20, implants 712 are being used to fuse two adjacent vertebrae 770a, 770b. As described above with respect to the dental implants 112, 212, the implants 712 are first positioned into the bone tissue. After the implant is properly positioned, the implant can be rotated or pulled distally to anchor the projections 732 in the bone tissue. After the implants 712 are properly installed in the bone, the two vertebrae 770a, 770b, can be secured to each other by attaching a bracket 772 to the implants with screws 774. The implants 712 can be used in a variety of other orthopedic procedures. Furthermore, a variety of other mechanical fasteners and/or adhesives can be use to secure implants 712 to each other without departing from the scope of the invention.

The invention claimed is:

1. A dental implant system for supporting a cosmetic tooth prosthesis, the dental implant system comprising:
   an elongated body adapted to be disposed in a jaw bone of a patient and including a proximal end and a distal end, the elongated body having a longitudinal axis extending between the proximal and distal ends, an outer surface of the elongated body including a plurality of projections radially disposed around the outer surface, each of the plurality of projections configured to move from an undeployed configuration in which the projections are generally flush against the outer surface and are disposed on the outer surface to a deployed configuration in which the projections extend outwardly from the outer surface for anchoring the elongated body into tissue in the jaw bone, wherein the elongated body defines a threaded bore extending distally from the proximal end thereof;
   a collar disposed adjacent the proximal end of the elongate body and having the threaded bore extending therethrough; and
   an actuating component configured to be inserted into the threaded bore so that the projections are configured to move from the undeployed configuration to the deployed configuration when the actuating component is first moved distally and then moved proximally relative to the elongated body,
   wherein the projections are disposed on the outer surface of the elongated body in the undeployed configuration until the actuating component is moved distally and then proximally relative to the elongated body.

2. The dental implant system of claim 1, wherein the outer surface tapers along the longitudinal axis distally from the proximal end of the elongated body.

3. The dental implant system of claim 1, wherein the plurality of projections extend unidirectionally from the outer surface of the elongated body.

4. The dental implant system of claim 1, wherein the plurality of projections are arranged as a plurality of longitudinally aligned groups with the groups disposed circumferentially around the elongated body.

5. The dental implant system of claim 1, wherein the threaded bore is configured to receive an abutment that is configured to receive the cosmetic tooth prosthesis.

6. The dental implant system of claim 1, further comprising:
   an abutment configured to be coupled with the elongated body, the abutment including a post configured to receive the cosmetic tooth prosthesis.

7. The dental implant system of claim 6, wherein the abutment includes a threaded screw member for screwing into the threaded bore defined by the elongated body member.

8. The dental implant system of claim 6, wherein the abutment includes a cylindrical base portion and the post is coupled to the cylindrical base portion.

9. The dental implant system of claim 8, wherein the cylindrical base portion includes a plurality of apertures to allow cleaning of the cosmetic tooth prosthesis.

10. The dental implant system of claim 1, wherein the collar is configured to receive a distal end of an abutment configured to support the cosmetic tooth prosthesis.

11. The dental implant system of claim 1, wherein at least one of the outer surface of the elongated body and the plurality of projections comprise features configured to promote osseointegration.

12. The dental implant system of claim 11, wherein the features comprise macroscopic structures configured to promote osseointegration.

13. The dental implant system of claim 11, wherein the features comprise mechanical texturing, physical texturing, and/or a coating with a substance.

14. The dental implant system of claim 13, wherein the mechanical or physical texturing comprises acid-etching, grit blasting, or bead blasting.

15. A dental implant system for supporting a cosmetic tooth prosthesis, the dental implant system comprising:

an elongated body adapted to be disposed in a jaw bone of a patient and including a proximal end and a distal end, the elongated body having a longitudinal axis extending between the proximal and distal ends, an outer surface of the elongated body including a plurality of projections radially disposed around the outer surface, each of the plurality of projections configured to move from an undeployed configuration in which the projections are generally flush against the outer surface of elongated body to a deployed configuration in which the projections extend outwardly from the outer surface for anchoring the elongated body into tissue in the jaw bone, wherein the elongated body defines a threaded bore extending distally from the proximal end thereof; and an actuating mechanism configured to be inserted into the threaded bore to deploy the plurality of projections from within the threaded bore so that axial movement of the actuating mechanism distally and then proximally relative to the elongated body causes the plurality of projections to move between the undeployed and deployed configurations.

* * * * *